United States Patent [19]

Revesz

[11] Patent Number: 4,912,114

[45] Date of Patent: Mar. 27, 1990

[54] MORPHINAN DERIVATIVES

[75] Inventor: Laszlo Revesz, Riehen, Switzerland

[73] Assignee: Sandoz Ltd., Basle, Switzerland

[21] Appl. No.: 338,905

[22] Filed: Apr. 14, 1989

Related U.S. Application Data

[63] Continuation of Ser. No. 169,923, Mar. 18, 1988, abandoned, which is a continuation of Ser. No. 864,391, May 19, 1986, abandoned.

[51] Int. Cl.$^4$ ............... A61K 31/485; C07D 489/02; C07D 221/28
[52] U.S. Cl. .................... 514/282; 514/289; 546/39; 546/44; 546/45; 546/46; 546/74
[58] Field of Search ............ 546/39, 44, 45, 46, 546/74; 514/282, 289

[56] References Cited

U.S. PATENT DOCUMENTS

| | | | |
|---|---|---|---|
| 3,488,354 | 1/1970 | Brown et al. | 546/45 |
| 4,148,794 | 4/1979 | Lewis et al. | 546/74 |
| 4,208,523 | 6/1980 | Michne et al. | 546/97 |
| 4,217,353 | 8/1980 | Smith Jr. | 514/282 |
| 4,255,579 | 3/1981 | Michne | 546/74 X |

FOREIGN PATENT DOCUMENTS

| | | |
|---|---|---|
| 3617182 | 11/1986 | Fed. Rep. of Germany . |
| 1154505 | 6/1969 | United Kingdom ............ 546/39 |

OTHER PUBLICATIONS

Belleau, Chemical Abstracts, vol. 98(9):65101b (1982).
Fleischacker, et al., Monatshefte für Chemie, vol. 108, pp. 1441-1451 (1977).
Fleischacker, et al., Chem. Ber., vol. 112, pp. 2539-2551 (1979).
Bentley, et al., J. Am. Chem. Soc., vol. 89(13), pp. 3293-3303 (1967).
Lewis, et al., J. Med. Chem., vol. 16(1), pp. 9-12 (1973).
Lewis, et al., Chemical Abstracts, vol. 68:69164c (1968).
Bentley, et al., J. Org. Chem., vol. 23, pp. 1720-1725 (1958).
Besser, et al., Opioid Modulation of Endocrine Function, pp. 99-109 (1984).
Delitala, et al., Opioid Modulation of Endocrine Function, pp. 65-79 (1984).
Ferin, M., Opioid Modulation of Endocrine Function, pp. 185-189 (1984).
Meites, et al., Life Science, vol. 24, pp. 1325-1336 (1979).
Morley, J. E., Endocrine Reviews, vol. 8, No. 3, 256-287 (1987).
Atkinson, R. L., Jour. of Clin. Endocr. and Metab., vol. 55, No. 1, pp. 196-198 (1982).
Morley, et al., Science, vol. 209, pp. 1259-1261 (1980).
Thompson, et al., Life Sciences, vol. 31, pp. 847-852 (1982).
Holaday, et al., Nature, vol. 275, pp. 450 and 451 (1978).

(List continued on next page.)

Primary Examiner—Mukund J. Shah
Assistant Examiner—Diane G. Rivers
Attorney, Agent, or Firm—Gerald D. Sharkin; Robert S. Honor; Joseph J. Borovian

[57] ABSTRACT

Compounds of formula I wherein
X and Y each denotes hydrogen or together denote -O-,
$R_1$ denotes allyl optionally substituted by 1 to 3 alkyl groups, the substituent or substituents having in total a maximum of 3 carbon atoms, cyclopropylmethyl or 3-furylmethyl,
$R_2$ denotes hydrogen, alkyl with 1 to 10 C-atoms, cycloalkyl with 5 or 6 carbon atoms, optionally substituted phenyl or optionally substituted phenyl-alkyl with 7 to 12 C-atoms,
$R_3$ denotes hydrogen, alkyl with 1 to 10 C-atoms or phenyl,
$R_4$ denotes hydrogen, OH, $NR_6R_7$, NHCOR, $NHSO_2R'$ or NHCOOR'',
$R_6$ and $R_7$, independently of one another, denote hydrogen or alkyl with 1 to 3 C-atoms,
R denotes alkyl with 1 to 6 C-atoms, phenyl or —A—COOR'',
A denotes alkylene or alkenylene each with 2 to 4 C-atoms,
R' denotes alkyl with 1 to 6 C-atoms or phenyl,
R'' denotes methyl or ethyl
and wherein either $R_3$ is in the α-position and $R_4$ is in the β-position, or $R_3$ is in the β position and $R_4$ is in the α-position, or
$R_3$ and $R_4$ together are =O, or =$CH_2$, and
$R_5$ denotes hydrogen or methyl,
with the provisos that when X and Y denotes —O—, $R_2$ denotes hydrogen, $R_4$ denotes a αOH group and $R_3$ and $R_5$ denote hydrogen, then $R_1$ is other than cyclopropylmethyl of allyl,
and that when $R_2$, $R_3$, $R_4$ and $R_5$ are each hydrogen, $R_1$ is other than cyclopropymethyl,
in free base from or in acid addition salt form, as well as the physiologically hydrolyzable, pharmaceutically acceptable esters of such compounds, which contain a free OH group, in free base form or in acid addition salt form.

The compounds according to the invention are opiate agonists/antagonists and LH secretion stimulators.

19 Claims, No Drawings

OTHER PUBLICATIONS

Peters, et al., The Lancet, pp. 529–532 (1981).
Kosten, et al., Life Sciences, vol. 39, pp. 55–59 (1986).
Bain, et al., Life Sciences, vol. 40, pp. 1119–1125 (1987).
Kiianmaa, et al., Psychopharmacology, vol. 79, pp. 291–294 (1983).
Hynes, et al., Life Sciences, vol. 33, pp. 2331–2337 (1983).
Reisberg, et al., New England Jour. of Medicine, vol. 308, pp. 721 and 722 (1983).
Kaiya, et al., Life Sciences, vol. 33, pp. 1039–1043 (1983).
Banks, et al., The Lancet, pp. 1227–1230 (1983).
Derwent Abstract No. 3819c.
Derwent Abstract No. 38194C.
Derwent Abstract No. 56852C.
Derwent Abstract No. 70322E.

MORPHINAN DERIVATIVES

This is a continuation of application Ser. No. 07/169,923, filed Mar. 18, 1989 which in turn is a continuation of application Ser. No. 06/864,391, filed May 19, 1986, both now abandoned.

This invention relates to morphinan, including morphine, derivatives.

The present invention provides compounds of formula I wherein

X and Y each denotes hydrogen or together denote —O—, $R_1$ denotes allyl optionally substituted by 1 to 3 alkyl groups, the substituent or substituents having in total a maximum of 3 carbon atoms, cyclopropylmethyl or 3-furylmethyl, $R_2$ denotes hydrogen, alkyl with 1 to 10 C-atoms, cycloalkyl with 5 or 6 carbon atoms, optionally substituted phenyl or optionally substituted phenylalkyl with 7 to 12 C-atoms, $R_3$ denotes hydrogen, alkyl with 1 to 10 C-atoms or phenyl, $R_4$ denotes hydrogen, OH, $NR_6R_7$, NHCOR, $NHSO_2R'$ or NH—COR'', $R_6$ and $R_7$, independently of one another, denote hydrogen or alkyl with 1 to 3 C-atoms, R denotes alkyl with 1 to 6 C-atoms, phenyl or —A—COOR'', A denotes alkylene or alkenylene each with 2 to 4 C-atoms, R' denotes alkyl with 1 to 6 C-atoms or phenyl, R'' denotes methyl or ethyl and wherein either $R_3$ is in the α-position and $R_4$ is in the β-position, or $R_3$ is in the β-position and $R_4$ is in the α-position, or $R_3$ and $R_4$ together are =O, =$CH_2$/and $R_5$ denotes hydrogen or methyl, with the provisos that when X+Y denotes —O—, $R_2$ denotes hydrogen, $R_4$ denotes a α-OH and $R_3$ and $R_5$ denote hydrogen, then $R_1$ is other than cyclopropylmethyl or allyl, and that when $R_2$, $R_3$, $R_4$ and $R_5$ are each hydrogen, $R_1$ is other than cyclopropylmethyl, in free base form or in acid addition salt form, as well as the physiologically hydrolyzable, pharmaceutically acceptable esters of such compounds, which contain a free OH group, in free base form or in acid addition salt form.

The compounds according to the invention may exist in free base form or in acid addition salt form which may be obtained from the free base forms in conventional manner and vice versa. Examples of acid addition salts are the hydrochlorides, hydrobromides, hydrogen maleates and hydrogen malonates.

The compounds according to the invention may be produced as follows:

(a) in order to produce a compound of formula Ia wherein $R'_1$ denotes cyclopropylmethyl or 3-furylmethyl, a compound of formula VII is brominated, the resultant compound, which contains a bromine atom in at least position 5, is dehydrobrominated to form a furan ring, and the product is debrominated, (b) in order to produce a compound of formula Ib the ketal group in a compound of formula X wherein Z and Z' denote alkyl with 1-3 C-atoms or together denote $(CH_2)_2$ or $(CH_2)_3$, is hydrolysed to an oxo group, (c) in order to produce a compound of formula Ic

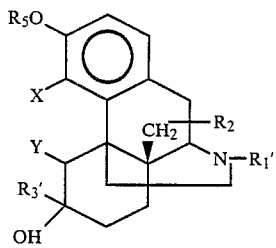

wherein R'₃ denotes alkyl with 1 to 10 C-atoms or phenyl, a compound of formula I'

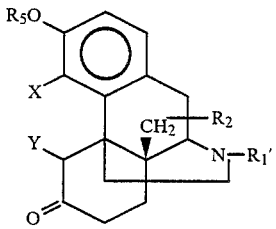

is reacted with an organic metal compound containing the radical R'₃, (d) in order to produce a compound of formula Id

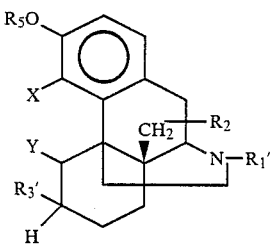

a compound of formula XI

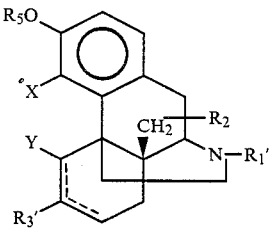

is reduced, (e) in order to produce a compound of formula Ie

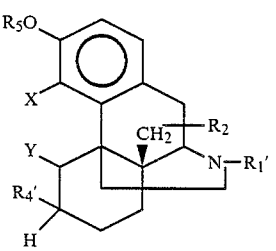

wherein R'₄ denotes NR₆R₇, NHCOR, NHSO₂R' or NH—COOR", a compound of formula I' is reductively aminated to form the corresponding 6-amino compound, and this latter compound is optionally alkylated or acylated on the N-atom, (f) in order to produce a compound of formula If

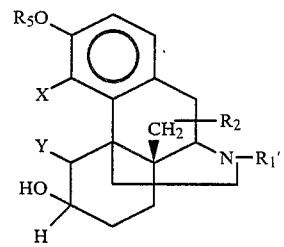

the oxo group in a compound of formula I' is reduced to a hydroxy group, (g) in order to produce a compound of formula Ig

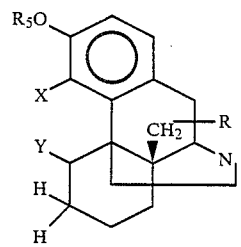

a compound of formula XII

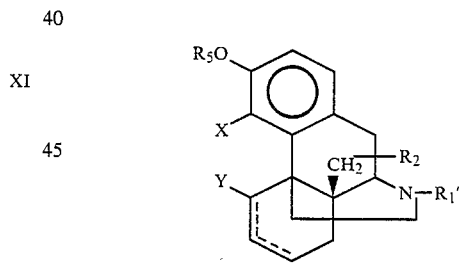

is reduced, (h) in order to produce a compound of formula Ih

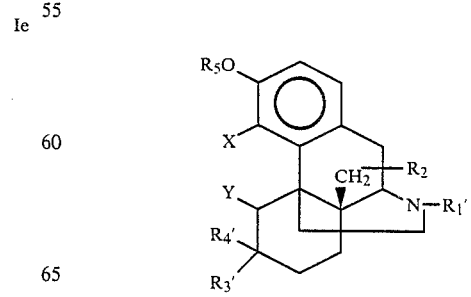

the benzyl group in a compound of formula XIII

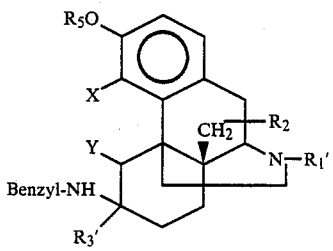

is removed hydrogenolytically, and the 6-amino compound obtained is optionally alkylated or acylated, (i) in order to produce a compound of formula Ii

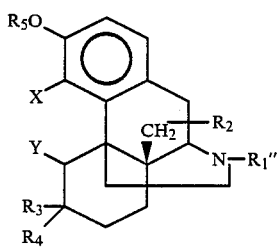

wherein R″₁ denotes allyl optionally substituted by 1 to 3 alkyl groups, the substituent or substituents having in total a maximum of 3 C-atoms, a compound of formula XIV

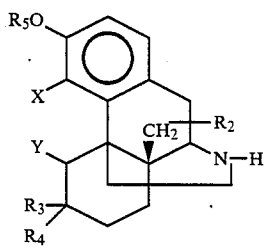

is reacted with a compound of formula R″₁X (X=halogen), (j) in order to produce a compound of formula Ij

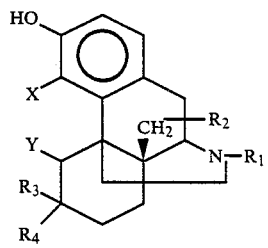

a compound of formula Ik

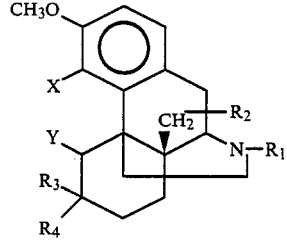

is subjected to an ether splitting, (k) in order to produce a compound of formula I wherein $R_3$ and $R_4$ together are $CH_2$, a compound of formula I wherein $R_3$ and $R_4$ together are O is reacted with $(C_6H_5)_3$ $P=CH_2$.

(l) in order to produce physiologically hydrolyzable and pharmaceutically acceptable esters of the compounds of formula I, which contain a free OH group, such a compound of formula I is reacted with an appropriate acid or with a reactive derivative thereof, or (m) to produce a compound of formula I wherein $R_4$ is $NR_6R_7$ wherein $R_6$ and $R_7$ are as defined above with the proviso that one of $R_6$ and $R_7$ is other than hydrogen, NHCOR, NHSO₂R' or NHCOOR", a compound of formula I wherein $R_4$ is $NR_6R_7$ wherein $R_6$ and $R_7$ are as defined above with the proviso that one of $R_6$ and $R_7$ is hydrogen/or $NH_2$ is alkylated or acylated respectively, wherein
in the above formulae the configurations of the group Y if present in the 5 position and the bonds linking the 9 and 13 positions are the same as in formula I, and the definitions of $R_1$ to $R_5$, X and Y except where otherwise stated are as given above with reference to formula I.

In the above formula, as well as in the description and the examples, and in intermediate and final products e.g. up to formulae XIV, the chiral carbon atoms have the configuration as in the natural (levorotatory) morphinan series i.e., in position 9:R; in position 13:R and in position 14:S. The present invention also covers compounds of formula I in admixture with e.g. their epimers, e.g. as in a racemic mixture.

The phenyl ring substituents include for example halogen, e.g. of atomic number from 9 to 53, $CF_3$, hydroxy, nitro, alkyl with 1 to 3 C-atoms, alkoxy with 1 to 3 C-atoms or $NR^aR^b$ wherein $R^a$ and $R^b$ independently are hydrogen or alkyl with 1 to 3 C-atoms.

Preferably mono substitution is present.
In the above formula preferably
$R_1$ is cyclopropylmethyl and/or
$R_2$ is alkyl, especially methyl or ethyl and/or
$R_2$ is cycloalkyl, especially cyclohexyl, and/or
$R_2$ is optionally substituted phenyl (e.g. phenyl or pHO-phenyl), and/or
$R_3$ is hydrogen, alkyl of 1 to 4 C-atoms or phenyl
$R_4$ is hydroxy or hydrogen, especially hydroxy and/or
$R_3$ and $R_4$ together are O or $CH_2$ and/or
$R_5$ is hydrogen.
Conveniently $R_3$ and $R_4$ together are O. Conveniently X and Y are each H. Preferably when $R_4$ is OH it is in the α-position.

All the reactions may be effected in conventional manner, or analogously to the examples given below. As mentioned above, process (a) may take place in 3 stages, firstly brominaton, e.g. with Br₂ in glacial acetic acid, then splitting of HBr in an alkaline medium, e.g. in NaOH solution, and finally removal by reduction of any Br atoms which are still present and have been introduced, e.g. into position 1 and 7 during the bromination of stage 1. This removal by reduction may take place e.g. by hydrogenation in the presence of pd/C.

Process (b) may be effected by means of hydrolysis in an acidic medium, e.g. in HCl solution.

Process (c) may be effected by reacting with a lithium organic compound, e.g. in ether.

The reduction processes (d) and (g) may be effected in a manner which is usual for the hydrogenation of double bonds, e.g. with Pd/C as a catalyst. Process (e) may be effected by methods which are known for amination by reduction, e.g. with boron hydride derivatives, such as $NaCNBH_3$, as reduction agents, in the presence of ammonium acetate. The subsequent optional alkylation or acylation and process (m) may take place in known manner, e.g. with alkyl or acid halides in the presence of a base e.g. in analogous manner to that described in Example 9.

The reduction of the oxo group to a hydroxy group (process (f) may take place in accordance with processes which are known for reduction, e.g. using $NaBH_4$ as a reducing agent.

The removal of the benzyl group from compounds of formula XIII (process h) may take place in the usual way, by hydrogenolysis, e.g. with Pd/C. Any subsequent reactions may take place as described for process (e).

Process (i) may be a conventional alkylation of secondary to tertiary amines.

The ether cleavage of process (j) may take place using the conventional reagents, such as HBr, $BBr_3$ or pyridine hydrochloride.

The process (k) may be effected in conventional manner known for Wittig reactions.

The acylation of process (l) may take place in conventional manner, e.g. with acid halides in the presence of a base.

The starting compounds of formula VII (process a) may be produced e.g. in accordance with the following scheme:

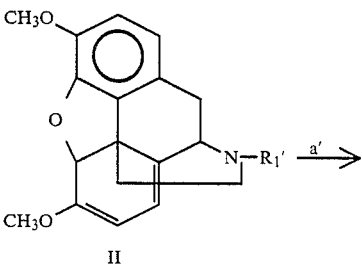

II

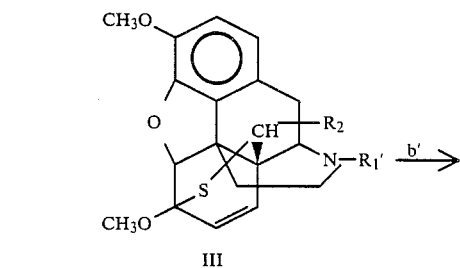

III

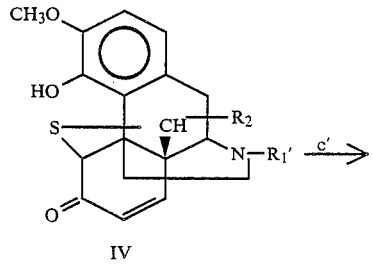

IV

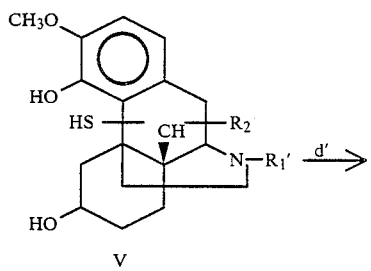

V

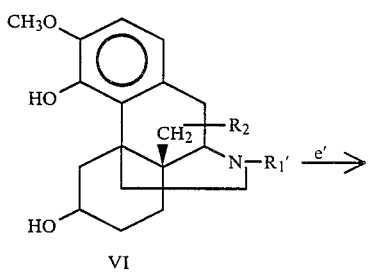

VI

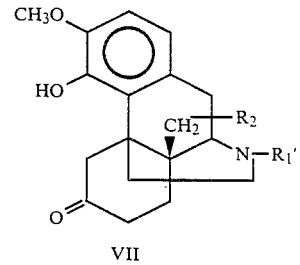

VII

Production of the compounds of formula III (process a') may take place by reacting a compound of formula II with thiosulphinate of formula

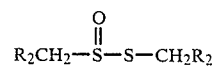

(Diels-Alder reaction) by heating them in an inert solvent, e.g. in toluene, under reflux.

Opening of the furan ring (with simultaneous changing of position of the S-atom) (process b') may be effected, e.g. through the action of HBr.

Opening of the S-ring (process c') in order to produce the compounds of formula V may be attained by reduction of the compounds of formula IV, with simultaneous saturation of the double bond and reduction of the oxo group, e.g. with Li in liquid ammonia.

Removal of the SH group from the compounds of formula V (process d') may be effected, e.g. with Raney-Nickel in methanol.

Finally, the 6-hydroxy group in the compounds of formula VI may be transformed into an oxo group (process e') in conventional manner, e.g. by reacting it with oxalyl dichloride and dimethyl sulphoxide.

Production of the compounds of formula VII, wherein $R_2$ denotes phenyl, may be effected directly from the compounds of formula III, by means of a reaction with Raney-Nickel in methanol.

The starting compounds of formula X (process b) may be produced from the compounds of formula VII in accordance with the following reaction scheme:

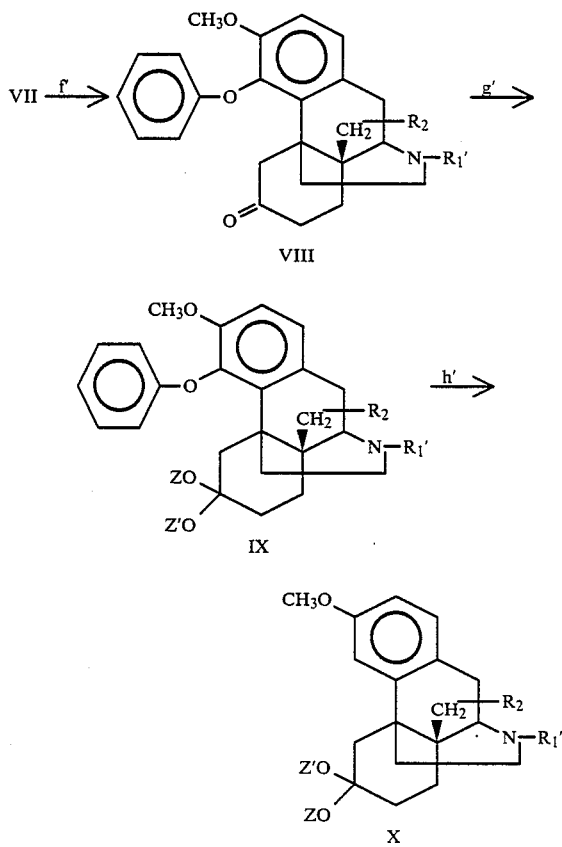

The compounds of formula VIII may be obtained by conventional etherification of the 4-hydroxy group with e.g. a halobenzene in the presence of a base and copper (process f').

In the compounds of formula VIII thus obtained, the 6-oxo-group may be then transformed into a ketal group (process g') in conventional manner, with an alcohol or glycol.

Finally, in the compounds of formula IX thus obtained, the 4-phenoxy group is removed by reduction (process h'), e.g. with Na in liquid ammonia.

The starting compounds XI and XII may be obtained by dehydration of the compounds of formulae Ic or If respectively. Dehydration may take place in the usual manner, e.g. by heating in an acidic medium, e.g. in HCl solution or in pyridine hydrochloride. Mixtures of 5,6 and 6,7-didehydro compounds are thus produced.

The starting compounds of formula XIII may be obtained by reacting the 6-oxo group in the compounds of formula I' with benzylamine to form the corresponding 6-benzylimine compounds, and further reacting the compounds thus obtained with a Grignard compound of formula $R'_3MgX$, with subsequent hydrolysis.

The starting compounds of formula XIV are obtainable by demethylation (e.g. with chloro-formic acid vinyl ester or cyanogen bromide) of the corresponding N-methyl compounds (these latter compounds may be produced analogously to the compounds of formula I according to the invention).

During the above-mentioned reactions, if compounds of formula I are obtained in which $R_3$ and $R_4$ have differing significances, they usually exist as mixtures of the 6α-$R_3$, 6β-$R_4$ and 6α-$R_4$, 6β-$R_3$ isomers, which can be separated into their components in conventional manner, e.g. by chromatography.

In reaction (c) and in the Grignard reaction to produce the starting compounds of formula XIII, the 6α-OH, 6β-$R'_3$ compounds or 6α-$NH_2$- 6β-$R'_3$ compounds respectively are primarily produced.

The present invention covers compounds of formula III to XIV per se.

Insofar as the production of any particular starting material is not particularly described, it is known or may be produced in conventional manner analogous to the examples.

The compounds of formula II are known. They can be produced from thebaine. The present invention also provides a process for the production of a compound of formula I wherein $R_3$ and $R_4$ together are oxygen which includes any of the following steps, in any order, of (i) replacing the 17-methyl group in thebaine by the group $R_1$, (ii) introducing the group $CH_2R_2$ into position 14, (iii) demethylating as appropriate to convert the methoxy groups in positions 3 and 6 into hydroxy and keto groups respectively, and (iv) if desired removing the oxygen bridge in the 4,5 position.

"Thebaine" includes any alkaloid of the thebaine series. These reactions may be effected in one or more steps as desired, e.g. along the lines indicated above with respect to processes (a) to (m) and (a') to (h') and e.g. step (iii) may for example involve a rearrangement.

Further reactions from e.g. one intermediate into another and from one compound of formula I into another may be made in conventional manner.

The following non-limitative examples illustrate the invention. Temperatures are in degrees Centigrade and are uncorrected.

In the examples maleinate=maleate.

EXAMPLE 1

17-cyclopropylmethyl-4,5α-epoxy-3-methoxy-14β-ethylmorphinan-6-one (a) 6,14-endo-etheno-6,7,8,14-tetrahydro-7-thia-8α-methyl-N-cyclopropylmethylnorthebaine 46.4 g (0.132 mols) of N-cyclopropylmethylnorthebaine and 17.6 g (0.128 mols) of S-ethylethanethiosulphinate are refluxed for 1 hour in 1000 ml of toluene, and after cooling are washed twice with water. The organic phase is dried over $Na_2SO_4$, concentrated, and flash-chromatographed over silica gel with methylene chloride/methanol/conc. $NH_3$ 99.5:5:0.1. The title compound is isolated as pale yellow crystals.

(b) N-cyclopropylmethyl-5,14-ethano-17α-methyl-18-thianorthebainone 40.6 g (0.099 mol) of the compound of stage (1a) are stirred at room temperature into 150 ml of 48% hydrobromic acid, whereby the starting material becomes completely dissolved. As soon as the reaction product starts to crystallize, 60 ml of methanol were added and stirred for one hour at 0° C. The hydrobromide of the title compound is filtered off and washed with methanol/ether: m.p.: 256°–258° C.

(c) N-cyclopropylmethyl-4,6α-dihydroxy-14β-(1-mercapto)ethyl-3-methoxymorphinan 4.3 g (0.62 mols) of lithium are dissolved at −45° C. in 1.8 l of liquid ammonia, and 22.5 g (56.7 mMols) of the compound of stage (1b) —dissolved in 500 ml of tetrahydrofuran—are added to the deep blue solution. After 20 minutes at −40° C., the solution is broken down with solid ammonium chloride, the ammonia is distilled off, the residue taken up in water and extracted three times with ether. After drying, concentrating and flash-chromatography with ethyl acetate/hexane (1:4 to 1:2), the organic phases yield the title compound as a colorless oil.

(d) N-cyclopropylmethyl-14β-ethyl-4,6α-dihydroxy-3-methoxymorphinan 130 g of Raney-Nickel are added to 1.5 l of methanol, and 13.4 g (33.3 mMol) of the compound of stage (1c) in 250 ml of methanol are rapidly added with vigorous stirring. After 15 minutes, the reaction mixture is filtered and concentrated by evaporation. The residue is taken up in methylene chloride, dried over $Na_2SO_4$, concentrated by evaporation, and the title compound is obtained as a light red foam.

(e) N-cyclopropylmethyl-14β-ethyl-4-hydroxy-3-methoxymorphinan-6-one 4.35 ml (50.4 mMol) of oxalyl chloride are added at −60° C. to 500 ml of methylene chloride, and mixed with 7.2 ml (100.7 mMol) of DMSO in 85 ml of methylene chloride. Then, 17 g (45.8 mMol) of the compound of stage (1d) in 100 ml of methylene chloride are rapidly added at −78° C., followed by 32 ml (229 mMol) of triethylamine at −60° to −50° C. after 15 minutes at −78° C. The reaction mixture is slowly heated to room temperature, water is added, and the mixture is extracted three times with methylene chloride. After drying, concentrating by evaporation and flash-chromatography with ethyl acetate/hexane (1:3 to 1:1), the organic phases yield the title compound as a colorless oil.

(f) 17-cyclopropylmethyl-4,5α-epoxy-3-methoxy-14β-ethylmorphinan-6-one 14.6 g (39.6 mMol) of the compound of stage (1e) are added to 430 ml of glacial acetic acid, and 19.0 g (119 mMol) of $Br_2$ in 200 ml of glacial acetic acid are added in drops whilst stirring at room temperature over the course of 30 minutes. After 90 minutes, the reaction mixture is concentrated by evaporation, taken up in 1 l of methylene chloride, and poured whilst stirring and cooling into 300 ml of 1N NaOH. The methylene chloride phase is separated, washed with water and a little 10% tartaric acid (pH 7), dried over $Na_2SO_4$ and concentrated. The remaining residue is dissolved in 170 ml of glacial acetic acid, and after adding 130 ml of water and 3 g of 10% Pd/C, the mixture is hydrogenated for 15 hours at room temperature and at 1 atm. The Pd/C is filtered off, the glacial acetic acid distilled off, the residue taken up in ice/2N $Na_2CO_3$ and extracted three times with methylene chloride. Drying of the organic phase over $Na_2SO_4$, concentration and flash-chromatography with ethyl acetate/hexane 1:5 yield the title compound as colorless crystals.

EXAMPLE 2

17-cyclopropylmethyl-4,5α-epoxy-14β-ethyl-3-hydroxymorphinan-6-one 3.25 g (8.9 mMol) of the compound of example 1 and 10 g of pyridine hydrochloride are heated for 3 hours to 190° C., then taken up in water after cooling, rendered basic with conc. ammonia, and extracted three times with methylene chloride. Flash-chromatography with ethyl acetate/hexane 1:5 yields the title compound as colorless crystals. Recrystallization from ether/pentane yields an analysis-pure product: M.p.: 157°–158° C.

EXAMPLE 3

14β-benzyl-17-cyclopropylmethyl-4,5α-epoxy-3-methoxymorphinan-6-one (a) 6,14-endo-etheno-6,7,8,14-tetrahydro-7-thia-8α-phenyl-N-cyclopropylmethylnorthebaine 40.4 g (0.115 mols) of N-cyclopropylmethylnorthebaine and 21 g (0.08 mols) of S-benzylphenylmethanethiosulphinate are refluxed for 1 hour in 750 ml of toluene. The reaction mixture is concentrated by evaporation, mixed with water, and extracted three times with ether. After drying and evaporating the ether phase, colorless crystals remain, which yield the title compound after washing with a little ether. M.p.: 148°–150° C.

(b) N-cyclopropylmethyl-3-methoxy-4-hydroxy-14β-benzylmorphinan-6-one 20 g (42.3 mMol) of the compound of stage (3a) and 200 g of Raney-Nickel are refluxed in 1.3 l of methanol for 4 hours, and after a further addition of 70 g of Raney-Nickel for a further 3 hours. The Raney-Nickel is filtered off and washed well with methanol. The combined methanol phases are concentrated, the remaining residue is taken up in ether and dried over $Na_2SO_4$, concentrated, and yields a colorless oil. Flash-chromatography over 350 g of silica gel with ethyl acetate/hexane 1:8 yields the title compound as colorless crystals. M.p.: 122°–124° C.

(c) 14β-benzyl-17-cyclopropylmethyl-4,5α-epoxy-3-methoxymorphinan-6-one 2.2 g (5.1 mMol) of the compound of stage (3b) are added to 70 ml of glacial acetic acid, and mixed with 2.45 g (15.3 mMol) of $Br_2$ in 30 ml of glacial acetic acid, stirred for 4 hours at room temperature and concentrated by evaporation. The remaining residue is taken up in methylene chloride, shaken out with 100 ml of 1N NaOH whilst cooling with ice, the organic phase is separated, shaken with water, and 10% tartaric acid is added until reaching a pH of 6. The organic phase is dried over $Na_2SO_4$ and concentrated, mixed with 200 ml of water/glacial acetic acid 1:1, then 4.2 g of sodium acetate and 0.75 g of 10% Pd/C are added, and the mixture is hydrogenated at 3 atm. and at room temperature. The reaction mixture is filtered, concentrated by evaporation, taken up in methylene chloride and washed with 2N soda. Drying and concentration of the organic phase yield a light yellow oil, which after flash-chromatography with ether/hexane 1:3 yields the title compound as a colorless oil.

EXAMPLE 4

14β-benzyl-17-cyclopropylmethyl-4,5α-epoxy-3-hydroxymorphinan-6-one 12.5 g of pyridine hydrochloride and 5.2 g (12 mMol) of the compound of example 3 are mixed at room temperature, and heated to 160° C. whilst stirring. After 1 hour, a further 12.5 g of pyridine hydrochloride are added, and heating continues for a further hour at 160° C. After cooling, the mixture is taken up in ice water, rendered basic with conc. ammonia and extracted three times with methylene chloride. The organic phases are dried over $Na_2SO_4$, concentrated by evaporation and flash-chromatographed over silica gel with ethyl acetate/hexane 1:3. The following are isolated: the title compound as a colorless oil and unreacted starting material. The title compound is converted into the hydrochloride with ether/ethanol/HCl: M.p.: 260° C.

EXAMPLE 5

N-cyclopropylmethyl-14β-benzyl-3-methoxymorphinan-6-one (a) N-cyclopropylmethyl-14β-benzyl-3-methoxy-4-phenoxymorphinan-6-one 8.9 g (19 mMol) of the compound of example (3b), 5 ml (48 mMol) of bromobenzene and 8.0 g (58 mMol) of $K_2CO_3$ are dissolved in 100 ml of pyridine, 2.0 g of Venus copper are added and heated for 16 hours under argon to 140° C. Ice water is added to the dark reaction mixture, which is extracted three times with ether. The organic phases are dried with $Na_2SO_4$, concentrated by evaporation, and yield the title compound as a dark oil which is reacted to form the next compound without further purification.

(b) N-cyclopropylmethyl-14β-benzyl-3-methoxy-4-phenoxy-6,6-ethylenedioxy-morphinan 9.2 g (18 mMol) of the compound of stage (5a), 30 ml (0.54 mol) of ethylene glycol and 9.4 g (50 mMol) of p-toluenesulphonic acid monohydrate are refluxed for 4 hours in a water separator in 1 l of benzene. The reaction mixture is washed once with 2N soda and once with water, dried over $Na_2SO_4$ and concentrated, and yields the title compound as a dark brown oil which is reacted to form the next compound without further purification.

(c) N-cyclopropylmethyl-14β-benzyl-3-methoxy-6,6-ethylenedioxymorphinan 9.7 g (17.6 mMol) of the compound of stage (5b) in 250 ml of toluene are added in drops to 500 ml of liquid ammonia which has been prepared at −55° C., and then 2.5 g (109 mMol) of sodium are added. The reaction mixture is stirred for 4 hours at −55° to −35° C., then broken down by adding solid ammonium chloride, and the ammonia is distilled off. The residue is taken up in water and extracted three times with ether. The ether phases are washed twice with 1N NaOH and once with water, dried over $Na_2SO_4$, concentrated, and after flash-chromatography yield the title compound as colorless crystals. $[\alpha]_D^{20} = -28.8°$ ($CH_3OH$). (d) N-cyclopropylmethyl-14β benzyl-3-methoxymorphinan-6-one 5.8 g (12.6 mMol) of the compound of stage (5c) were refluxed for 4 hours in 750 ml of 1N HCl, then mixed with ice/conc. ammonia after cooling, and extracted three times with ether. After drying and concentrating the organic phase, followed by recrystallization from ether, the title compound is obtained. M.p.: 165°–167° C.

EXAMPLE 6

N-cyclopropylmethyl-14β-benzyl-3-hydroxymorphinan-6-one 1.65 g (4 mMol) of the compound of example 5 and 8.6 g of pyridine hydrochloride are heated to 180° C., after one hour 8.6 g of pyridine hydrochloride are added, and the temperature is kept at 180° C. for a further hour. Ice/conc. ammonia is added to the reaction mixture, which is extracted three times with methylene chloride. After drying, concentrating and flash-chromatography (ethyl acetate/hexane 1:8), the combined organic phases yield the hydrochloride of the title compound. M.p.: 290° C. M.pt. (HBr salt)>280° C. $[\alpha]_D^{20}$ (free base)= −69.6° [$CH_3OH$].

EXAMPLE 7

17-cyclopropylmethyl-4,5α-epoxy-14β-ethyl-3,6α-dihydroxy-6β-methyl-morphinan 635 mg (1.8 mMol) of the compound of example 2 are added at 0° to 100 ml of ether, and then 14 ml (22.4 mMol) of a 1.6 molar solution of methyllithium in ether are added. The reaction mixture is slowly heated to room temperature, then broken down after 4 hours with 10% ammonium chloride solution, and extracted three times with methylene chloride. The organic phases are washed with conc. ammonia, dried over $Na_2SO_4$ and concentrated. After flash-chromatography with ethyl acetate/hexane 1:5, the residue yields the title compound as colorless crystals, together with unreacted starting material. Recrystallization from ether/hexane yields the analysis-pure title compound. M.p.: 199°–200° C.

EXAMPLE 8

17-cyclopropylmethyl-6α-amino-4,5α-epoxy-3-hydroxy-14β-ethylmorphinan and 17-cyclopropylmethyl-6β-amino-4,5α-epoxy-3-hydroxy-14β-ethylmorphinan 260 mg (4.13 mMol) of $NaCNBH_3$ in 10 ml of methanol are added in drops to a preparation at room temperature which consists of 1.5 g (4.25 mMol) of the compound of example 2 and 3.3 g (42.5 mMol) of ammonium acetate. After stirring for 17 hours at room temperature, the reaction mixture is adjusted to a pH of 1 with conc. hydrochloric acid, and is concentrated by evaporation. The residue is taken up in water, adjusted to a pH of 8 with 2N soda, and extracted three times with methylene chloride. After drying the organic phase over $Na_2SO_4$, concentrating by evaporation and flash-chromatography with methylene chloride/methanol/conc. ammonia (98:2:0.2 to 90:10:0.5), the two title compounds are isolated (firstly the 6β-isomer, and then the 6α-isomer).

EXAMPLE 9

17-cyclopropylmethyl-4,5α-epoxy-14β-ethyl-3-hydroxy-6β-[trans-3-methoxycarbonyl)acrylamido]-morphinan 426 mg (1 mMol) of the 6β-isomer of example 8 as the dihydrochloride are added at room temperature to a mixture of 20 ml of tetrahydrofuran, 10 ml of water and 600 mg (4.35 mMol) of $K_2CO_3$, and then a solution of 163 mg (1.1 mMol) of fumaric acid monomethylester chloride in 10 ml of tetrahydrofuran is slowly added whilst stirring. After 30 minutes, the reaction mixture is extracted three times with ethyl acetate, the organic phases are dried over $Na_2SO_4$ and concentrated by evaporation. After flash-chromatography (methylene chloride/methanol/conc. ammonia 99:1:0.1) and crystallization as the hydrochloride from ethanol, the residue yields the hydrochloride of the title compound. M.p.: >300° C. 17-cyclopropylmethyl-4,5α-epoxy-14β-ethyl-3-hydroxy-6α-[trans-3-(methoxycarbonyl)acrylamido]morphinan is produced in a similar way from the 6α-isomer of example 8. M.p.: 233°–236° C.

EXAMPLE 10

N-cyclopropylmethyl-14β-ethyl-3,6α-dihydroxy-6β-methylmorphinan 1.1 g (3.25 mMol) of N-cyclopropylmethyl-14β-ethyl-3-hydroxymorphinan-6-one (produced analogously to examples 5 and 6 from the compound of example (1e) are added at 0° to 130 ml of ether, and then mixed with 24.4 ml (39 mMol) of a 1.6 molar solution of methyllithium in ether. The reaction mixture is slowly heated to room temperature and stirred for 4 hours, mixed with 10 ml of 10% ammonium chloride solution, acidified to a pH of 1 with 3N HCl, rendered basic again with conc. ammonia, and extracted twice with ether. After drying over $Na_2SO_4$, the ether phases are concentrated, and after flash-chromatography (methylene chloride/methanol/conc. ammonia 98:2:0.2), the hydrogen malonate of the title compound is obtained. M.p.: 183°–184° C.

EXAMPLE 11

N-cyclopropylmethyl-14β-ethyl-3-hydroxy-6αmethyl-morphinan (a)
N-cyclopropylmethyl-14β-ethyl-6α-hydroxy-3-methoxy-6β-methylmorphinan 0.76 g (2.16 mMol) of N-cyclopropylmethyl-14β-ethyl-3-methoxymorphinan-6-one (produced analogously to example 5 from the compound of example (1e) are added at 0° to 100 ml of ether, and mixed whilst stirring with 16.3 ml of a 1.6 molar solution of methyllithium in ether. The reaction mixture is slowly heated to room temperature, and after 3 hours is broken down with 10 ml of a 10% ammonium chloride solution. The ether phase is separated, dried over $Na_2SO_4$, concentrated, and the title compound is obtained as a light yellow oil which is reacted to form the next compound without further purification.

(b) N-cyclopropylmethyl-5,6-(and 6,7)didehydro-14β-ethyl-3-hydroxy-6-methyl-morphinan 0.8 g (2.16 mMol) of the compound of stage 11a and 4 g of pyridine hydrochloride are heated to 180°, and a further 4 g of pyridine hydrochloride is added at intervals of 1½ hours. After 4½ hours and after cooling, ice/con. ammonia is added, and the mixture is extracted three times with ether. After drying and concentrating, the organic phases yield a green-brown oil, which after chromatography over silica gel (methylene chloride/methanol 98/2>95/5), yields a colorless oil. The proportion of the two olefins 5,6- or 6,7-didehydro is 5:1.

(c)
N-cyclopropylmethyl-14β-ethyl-3-hydroxy-6α-methyl-morphinan 0.45 g (1.33 mMol) of the compound of stage 11b are dissolved in 50 ml of glacial acetic acid and 25 ml of water, mixed with 0.3 g of Pd/C (10%) and hydrogenated for 15 hours at room temperature and at 3 atm. The reaction mixture is filtered, concentrated by evaporation, taken up in ice/10% ammonia solution and extracted three times with ether. The organic phase is dried, concentrated, and after chromatography over silica gel (methylene chloride/methanol/conc. ammonia 96/4/0.2), yields the title compound as a colorless oil which crystallizes as the hydrogen maleinate. M.p.: 203°–204° C.

EXAMPLE 12

N-cyclopropylmethyl-4,5α-epoxy-14β-ethyl-3,6β-dihydroxymorphinan

N-cyclopropylmethyl-4,5α-epoxy-14β-ethyl-3,6α-dihydroxymorphinan 0.92 g (2.6 mMol) of the compound of example 2 are dissolved in 100 ml of ethanol, mixed with 0.51 g (0.13 mols) of $NaBH_4$ and stirred at room temperature for 4 hours. By adding 30 ml of water and subsequently stirring for 30 minutes, the reaction mixture is broken down, the ethanol is distilled off, the remaining aqueous phase is firstly acidified with ice/3N HCl, then rendered basic again with conc. ammonia. The crystalline deposit is filtered off, recrystallized from ether, and the 6αhydroxy-isomer is obtained. M.p.: 299° C. (hydrochloride). The mother liquor is chromatographed over silica gel (methylene chloride/methanol/conc. ammonia 96/4/0.2), and the 6β-hydroxyisomer is obtained as a colorless oil. M.p.: 182°–184° C. (hydrogen maleinate).

EXAMPLE 13

N-cyclopropylmethyl-14β-ethyl-6β-hydroxy-3-methoxy-morphinan

N-cyclopropylmethyl-14β-ethyl-6α-hydroxy-3-methoxy-morphinan 0.95 g (2.7 mMol) of N-cyclopropylmethyl-14β-ethyl-3-methoxymorphinan-6-one (starting compound of example 11a) are dissolved in 70 ml of ethanol, then 0.53 g of $NaBH_4$ (0.14 mol) are added, and the mixture stirred for 3 hours at room temperature. The reaction mixture is stopped with 20 ml of water and subsequent stirring for 30 minutes. The ethanol is distilled off and the residue is extracted three times with methylene chloride. After drying and concentrating, the organic phase yields a colorless oil, which is separated by chromatography on silica gel (methylene chloride/methanol/conc. ammonia 99:1:0.1) into the two compounds named in the title. Both compounds are isolated as colorless oils.

EXAMPLE 14

14β-benzyl-N-cyclopropylmethyl-6β-hydroxy-3-methoxy-morphinan and

14β-benzyl-N-cyclopropylmethyl-6α-hydroxy-3-methoxy-morphinan

The above-mentioned compounds are produced analogously to example 13 from the compound of example 5.

EXAMPLE 15

14β-benzyl-N-cyclopropylmethyl-3,6β-dihydroxymorphinan 0.5 g (1.2 mMol) of the 6β-hydroxy-isomer of example 14 are heated to 180° C. together with 3.5 g of pyridine hydrochloride. After ever 1½ hours, an additional 2.5 g of pyridine hydrochloride are added. After a total of 4½ hours and a total of 8.5 g of pyridine hydrochloride, 10% aqueous ammonia is added, and the mixture is extracted three times with ether. After drying, concentrating and chromatography over silica gel (methylene chloride/methanol/conc. ammonia 95:5:0.25), the combined ether phases yield the title compound. M.p.: >280° C. (hydrochloride).

EXAMPLE 16

14β-benzyl-N-cyclopropylmethyl-3-hydroxymorphinan (a) 14β-benzyl-N-cyclopropylmethyl-5,6(and 6,7)-didehydro-3-hydroxymorphinan 0.8 g (1.92 mols) of the 6α-hydroxy-isomer of example 14 and 6 g of pyridine hydrochloride are heated to 180° C., and 6 g of pyridine hydrochloride are added again at intervals of 1½ hours. After a total of 5 hours and 18 g of pyridine hydrochloride, ice/conc. ammonia is added to the mixture, which is extracted three times with ether. The combined organic phases are dried, concentrated, and after chromatography over silica gel (methylene chloride/methanol/conc. ammonia 99:1:0.1), the title compound is obtained as a colorless oil.

(b) 14β-benzyl-N-cyclopropylmethyl-3-hydroxymorphinan 0.57 g (1.48 mMol) of the compound of stage (a) are dissolved in 60 ml of glacial acetic acid and 30 ml of water, then 0.4 g Pd/C (10%) are added, and the mixture is hydrogenated for 15 hours at room temperature and at 3-4 atm. The reaction mixture is filtered, concentrated, mixed with ice/conc. ammonia and extracted three times with ether. After drying, concentrating and chromatography over silica gel (methylene chloride/methanol/conc. ammonia 98:2:0.2), the organic phases yield the title compound as a colorless oil. M.p.: >280° C. (hydrochloride).

The following compounds of formula I, in which $R_1$ denotes cyclopropylmethyl and $R_5$ denotes hydrogen, were produced analogously to the above examples, from corresponding starting compounds. (In the table malonate=hydrogen malonate).

| Example no. | $R_2$ | $R_3$ | $R_4$ | X Y | m.p. | (salt form) | production analogous to example no. |
|---|---|---|---|---|---|---|---|
| 17 | $C_2H_5$ | =O | | —O— | >280° | HCl | 1 and 2 |
| 18 | H | =O | | —O— | 150-1° | Base | 1 and 2 |
| 19 | $CH_3$ | =O | | H H | >280° | HCl | 5 and 6 |
| 20 | Phenyl | H | α-OH | —O— | >300° | HCl | 12 |
| 21 | $CH_3$ | H | α-OH | H H | 233-5° | Base | 15 |
| 22 | $CH_3$ | H | β-OH | H H | 250°(decomp) | HCl | 15 |
| 23 | $C_2H_5$ | H | α-$NH_2$ | —O— | — | — | 8 |
| 24 | $C_2H_5$ | H | β-$NH_2$ | —O— | — | — | 8 |
| 25 | $C_2H_5$ | H | α-NHCOCH=CH—$COOCH_3$ | —O— | 211-2° | Base | 9 |
| 26 | $C_2H_5$ | H | β-NHCOCH=CH—$COOCH_3$ | —O— | 175-7° | Malonate | 9 |
| 27 | $C_2H_5$ | H | α-$NHCOCH_2$—$CH_2$—$COOCH_3$ | —O— | 249-51° | HCl | 9 |
| 28 | $C_2H_5$ | H | β-$NHCOCH_2$—$CH_2COOCH_3$ | —O— | 222-3° | Base | 9 |
| 29 | $CH_3$ | H | α-$NH_2$ | H H | — | — | 8 |
| 30 | $CH_3$ | H | β-$NH_2$ | H H | — | — | 8 |
| 31 | $CH_3$ | H | α-NHCOCH=CH—$COOCH_3$ | H H | >290° | HCl | 9 |
| 32 | $CH_3$ | H | β-NHCOCH=CH—$COOCH_3$ | H H | >290° | HBr | 9 |
| 33 | $CH_3$ | H | H | H H | 176-7° | Malonate | 16 |
| 34 | Phenyl | β-$CH_3$ | α-OH | —O— | >300° | HCl | 7 |
| 35 | $C_2H_5$ | β-$CH_3$ | α-OH | —O— | 250°(decomp) | HCl | 7 |
| 36 | $C_2H_5$ | α-$CH_3$ | β-OH | —O— | >280° | HCl | 7 |
| 37 | $C_2H_5$ | β-n-$C_4H_9$ | α-OH | —O— | 179-80° | Base | 7 |
| 38 | $C_2H_5$ | β-Phenyl | α-OH | —O— | 266-8° | HCl | 7 |
| 39 | Phenyl | H | α-OH | H H | >280° | HCl | 12 |
| 40 | Phenyl | β-n-$C_4H_9$ | α-OH | —O— | 93-112° | Base | 7 |
| 41 | Phenyl | β-Phenyl | α-OH | —O— | 174-182° | Base | 7 |
| 42 | -OH-Phenyl | =O | | H H | >230° | HCl | 2,6 |
| 43 | Cyclohexyl | =O | | H H | >265° | HCl | 1,2 |
| 44 | Phenyl | β-Phenyl | α-OH | H H | 240-265° | HCl | 7 |

EXAMPLE 45

N-Cyclopropylmethyl-14β-benzyl-3-hydroxy-6-methylene morphinan 760 mg of NaH are washed with dry pentane; 6 ml DMSO are added, the mixture heated for 30 min. at 80° C., then cooled to 0° C. 63 g of methyltriphenylphosphoniumbromide are dissolved in 12 ml DMSO and added to this solution. After 15 min. at room temperature 1 g of N-cyclopropylmethyl-14β-benzyl-3-hydroxy morphinan-6-one in 6 ml DMSO are added and the reaction mixture stirred at 60° for 12 hours. Ice and 10% NH$_4$Cl solution are added until pH 7, then the solution is extracted 3 times with ether. Evaporation of the solvent and flash chromatography with ethylacetate/hexane 1:8 gives the title compound, which is crystallized as hydrochloride salt from acetone. M.pt. 212° C.

The compounds of formula I exhibit pharmacological activity, and therefore are useful as pharmaceuticals.

In particular, the compounds have morphine-antagonistic or mixed morphine-agonistic/morphine-antagonistic activity.

The morphine-antagonistic activity was shown as follows: Female or male mice having a weight of 20-25 g are used in this test. 30 minutes prior to the treatment, the mice are immobilized in special plexiglass tubes, from which the tails protrude and can move freely. Using a lamp of high density, a pointed thermal stimulus is then attached 35 mm cranially to the root of the tail. The response is a swinging movement of the tail. The latent period (time between the stimulus and the response) is determined 30 and 15 minutes prior to intracerebrovascular application of the test substance. Morphine (5.6 mg/kg) is administered s.c. two minutes after the test substance. This dosage is sufficient to induce analgesic activity in 80-100% of the mice (prolonging of the latent period of 75% or more). The latent period is then determined again 30 minutes after administering the morphine (32 minutes after the test substance). The compounds lessen the analgesic activity of morphine at doses of from about 0.5 to about 30 mg/kg p.o.

The morphine-agonistic activity is shown as analgesic activity, for example in the arthritis pain test (based on the test described by A. W. Pricio et al. in Eur. J. Pharmacol. 31, 207-15, 1975).

The compounds of formula I are generally morphine antagonists, but the morphine-agonistic activity can be greatly increased by an appropriate choice of the substituent R$_4$. For example, compounds of formula I in which R$_1$ denotes cyclopropylmethyl and R$_4$ denotes a NHCO—A—COOR" radical show marked analgesic activity.

In general, the morphine agonists/antagonists show analgesic activity in the above-mentioned arthritis pain test in the rat at doses of 0.5 to 30 mg/kg body weight p.o.

Because of their analgesic activity, the substances are indicated for the treatment of pain of various origins.

The compounds of formula I which have morphine-antagonistic activity, especially those wherein R$_4$ is H or OH, or wherein R$_3$ and R$_4$ are together O or CH$_2$, also stimulate secretion of luteinizing hormone (LH). This LH stimulation can be determined e.g. by decapitating adult male rats 15 minutes to 3 hours, e.g. 1 hour, after administering the test substance, and measuring the LH concentration in the serum by radio-immunoassay. In this test, the compounds are active from ca. 1 to 30 mg/kg p.o. The compounds of formula I in which R$_2$ denotes phenyl show particularly strong LH stimulation.

The compounds are therefore useful as opiate agonists/antagonists and especially the compounds wherein R$_4$ is H or OH or wherein R$_3$ and R$_4$ are together O or CH$_2$ luteinizing hormone stimulators. The compounds are indicated for use in indications where luteinizing hormone stimulating activity is required, for example, due to impairment of the hypothalmic LHRH function, such as anovulatory syndrome, amenorrhea, infertility, idiophatic hypogonadotrophic hypogonadism, secondary hypothalmic hypogonadism, Kallman's syndrome, delayed puberty, menstrual disorders, e.g. during adolescence and anorexia nervosa. On the basis of opiate antagonist activity, the compounds are indicated for use in obesity, drug addiction, alcohol intoxication, motor disorders, cardiogenic and endotoxic shock, cognitive disorders such as Alzheimer's disease, and immune system modulation.

The LH stimulating indication is the preferred indication.

The example 6 compound is the preferred compound

For all these indications, the exact dosage will of course vary depending upon the compound employed, mode of administration and treatment desired.

In general, satisfactory results are obtained when administered at a daily dosage of from about 0.2 to about 30 mg/kg animal body weight.

For the larger mammals an indicated daily dosage is in the range from about 10 mg to about 100 mg of the compound conveniently administered in divided doses 2 to 4 times a day in unit dosage form containing for example from about 2 mg to 50 mg of the compound or in sustained release form.

The suitable daily dose for a particular compound will depend on a number of factors such as its relative potency to a standard in the indication, for example, naltrexone in the LH stimulating indication.

In an experiment with the preferred compound of example 6 at a dose of 5.6 mg/kg p.o. in the adult male rat in the LH stimulation test specified above produced a rise in serum LH levels 1 hour after administration to ca 80 mg/ml (control value ca 30 mg/mg). The standard naltrexone produced a rise in serum LH levels to ca 70 mg/kg.

In another experiment with the compound of example 4, serum LH levels in the same manner were measured as follows: at 1 mg/kg p.o.–50 mg/ml; at 3.2 mg/kg p.o.–54 mg/kg, at 10 mg/kg p.o.–68 mg/kg; at 32 mg/kg p.o.–75 mg/kg, (control value 34 mg/kg). In a further experiment in the same manner, the compound of example 4 to 32 mg/kg p.o. produced a serum LH concentration of 148 mg/kg (control value 44 mg/kg). The standard naltrexone produced a rise to 93 mg/kg at the same dose.

It is therefore indicated that the compounds of examples 4 and 6 may be administered at similar or lower doses than conventionally employed for naltrexone. Indicated doses are about 10 to 30 mg a day for larger mammals.

Furthermore, the example 27 compound has an ED$_{50}$ of 1 mg/kg p.o. in the analgesic arthritis pain test mentioned above compared to paracetamol with an ED$_{50}$ of 174 mg/kg p.o. On this basis it is indicated that the example 27 compound will be administered to larger mammals in correspondingly lower doses than paracetamol.

The compounds of the invention may be administered in free base form or in pharmaceutically acceptable acid addition salt form. Such salts may be prepared in conventional manner and exhibit the same order of activity as the free base form. The present invention also provides a pharmaceutical composition comprising a compound of the invention in free base form or in pharmaceutically acceptable acid addition salt form in association with a pharmaceutical carrier or diluent. Such compositions may be formulated in conventional manner.

The compounds may be administered by any conventional route, in particular enterally preferably orally e.g. in the form of tablets or capsules, or parenterally e.g. in the form of injectable solutions or suspensions.

A group of compounds are those wherein $R_2$ is hydrogen, alkyl with 1 to 10 C-atoms, phenyl or phenylalkyl with 7 to 12 C-atoms and $R_3$ and $R_4$ are as defined above with the proviso that $R_3$ and $R_4$ together are other than $CH_2$, in free base or in acid addition salt form.

In a first group of compounds $R_1$ is optionally substituted allyl.

In a 2nd group of compounds $R_1$ is cyclopropylmethyl.

In a 3rd group of compounds $R_1$ is 3-furylmethyl.

In a 4th group of compounds $R_2$ is H.

In a 5th group of compounds $R_2$ is alkyl.

In a 6th group of compounds $R_2$ is cycloalkyl.

In a 7th group of compounds $R_2$ is optionally substituted phenyl.

In a 8th group of compounds $R_2$ is optionally substituted phenylalkyl.

In a 9th group of compounds $R_3$ is H.

In a 10th group of compounds $R_3$ is alkyl.

In a 11th group of compounds $R_3$ is phenyl.

In a 12th group of compounds $R_4$ is H.

In a 13th group of compounds $R_4$ is OH.

In a 14th group of compounds $R_4$ is $NR_6R_7$.

In a 15th group of compounds $R_4$ is NHCOR.

In a 16th group of compounds $R_4$ is $NHSO_2R'$.

In a 17th group of compounds $R_4$ is NH—COOR".

In a 18th group of compounds $R_3$ is in the $\alpha$ position.

In a 19th group of compounds $R_3$ is in the $\beta$ position.

In a 20th group of compounds $R_3$ and $R_4$ are O.

In a 21st group of compounds $R_3$ and $R_4$ are $CH_2$.

In a 22nd group of compounds $R_5$ is $CH_3$.

In a 23rd group of compounds $R_5$ is H.

What we claim is:

1. A compound of formula I:

[Structure I]

wherein each of X and Y is hydrogen or, X and Y together are —O—;

$R_1$ is unsubstituted allyl; allyl, mono-, di- or tri-substituted by alkyl, said alkyl or alkyl groups having in total a maximum of 3 carbon atoms; cyclopropylmethyl or 3-furylmethyl;

$R_2$ is ethyl; cyclohexyl; phenyl or hydroxyphenyl;

$R_3$ is hydrogen; $C_1$–$C_{10}$alkyl or phenyl;

$R_4$ is hydrogen; hydroxy; $NR_6R_7$; NHCOR; $NHSO_2R'$ or NHCOOR";

$R_6$ and $R_7$, independently, are hydrogen or $C_1$–$C_3$ alkyl;

R is $C_1$–$C_6$alkyl; phenyl or —A—COOR";

R' is $C_1$–$C_6$alkyl or phenyl;

R" is methyl or ethyl; and

A is $C_2$–$C_4$alkylene or alkenylene;

and wherein either $R_3$ is in the $\alpha$-position and $R_4$ is in the $\beta$-position, or $R_3$ is in the $\beta$-position and $R_4$ is in the $\alpha$-position, or $R_3$ and $R_4$ together are =O or =$CH_2$; and $R_5$ is hydrogen or methyl;

which compound is in free base form or in acid addition salt form and, when said compound contains a free OH group, a physiologically, hydrolyzable pharmaceutically acceptable ester of said compound, which ester is in free base form or in acid addition salt form.

2. A compound of claim 1 wherein $R_1$ is cyclopropylmethyl in free base or in acid addition salt form.

3. A compound of claim 1 which is N-cyclopropylmethyl-14$\beta$-benzyl-3-hydroxymorphinan-6-one in free base or in acid addition salt form.

4. A method of inducing an opiate antagonist or agonist effect in a subject which method comprises administering an effective amount of compound of claim 1 to a subject in need of such treatment.

5. A pharmaceutical composition useful in inducing an opiate antagonist or agonist effect and in stimulating the secretion of luteinizing hormone comprising a pharmaceutically acceptable carrier or diluent and a therapeutically effective amount of a compound of claim 1, which compound is in free base form or in acid addition salt form and, when said compound contains a free OH group, a physiologically, hydrolyzable pharmaceutically acceptable ester of said compound, which ester is in free base form or in acid addition salt form.

6. A method of stimulating the secretion of luteneizing hormone in a subject which method comprises administering an effective amount of a compound of claim 1 to a subject in need of such treatment.

7. A compound selected from the group having the formulae III–X as depicted below:

[Structure III]

[Structure IV]

-continued

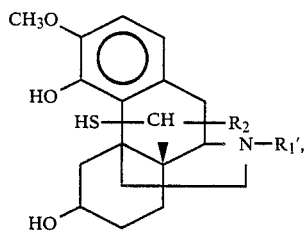
V

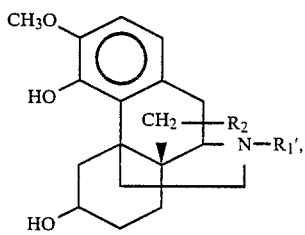
VI

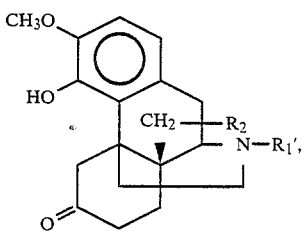
VII

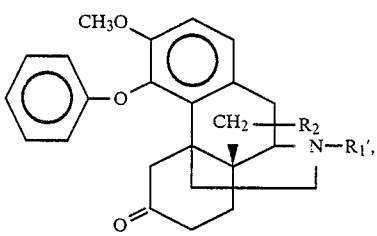
VIII

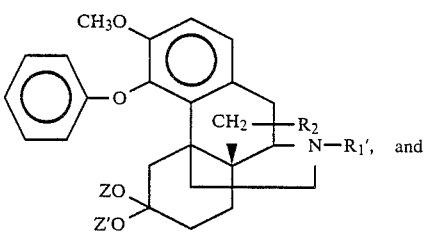
IX

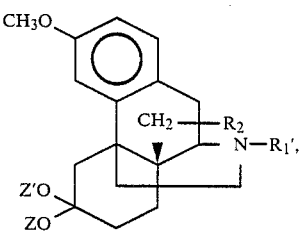
X wherein
R'₁ is cyclopropylmethyl or 3-furylmethyl;
R₂ is ethyl, cyclohexyl, phenyl or hydroxyphenyl; and
each of Z and Z' is, independently, C₁-C₃alkyl or, Z and Z', together are (CH₂)₂ or (CH₂)₃;
and wherein the configuration of the chiral carbon atoms in positions 5-, 9- and 13- are as in thebaine.

8. A compound selected from the group having the formulae XI-XIV as depicted below:

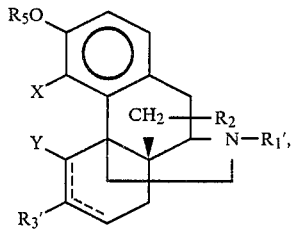
XI

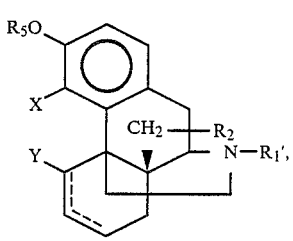
XII

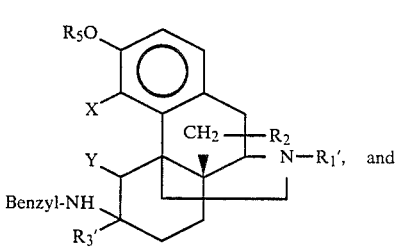
XIII

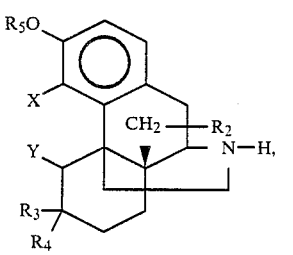
XIV wherein
R'₁ is cyclopropylmethyl of 3-furylmethyl;
R₂ is ethyl, cyclohexyl, phenyl or hydroxyphenyl;
R'₃ is C₁-C₁₀ or phenyl;
R₅ is hydrogen or methyl;
each of X and Y is hydrogen or, X and Y, together are —O—;
R₃ is hydrogen, C₁-C₁₀alkyl or phenyl;
R₄ is hydrogen; hydroxy; NR₆R₇; NHCOR; NHSO₂R' or NHCOOR";
R₆ and R₇, independently, are hydrogen or C₁-C₃alkyl;
R is C₁-C₆alkyl; phenyl or —A—COOR";
R' is C₁-C₆alkyl or phenyl;
R" is methyl or ethyl; and
A is C₂-C₄alkylene or alkenylene;
and wherein either R₃ is in the α-position and R₄ is in the β-position, or R₃ is in the β-position and R₄ is in the α-position, or R₃ and R₄ together are =O or =CH₂.

9. A compound of claim 1 where X and Y together are —O—, R₁ is cyclopropylmethyl, R₂ is ethyl, R₃ and R₄ together are =O, and R₅ is hydrogen, which compound is in free base or acid addition salt form.

10. A compound of claim 1 where X and Y together are —O—, $R_1$ is cyclopropylmethyl, $R_2$ is ethyl, $R_3$ is hydrogen, $R_4$ is α-amino, and $R_5$ is hydrogen, which compound is in free base or acid addition salt form.

11. a compound of claim 1 where X and Y together are —O—, $R_1$ is cyclopropylmethyl, $R_2$ is ethyl, $R_3$ is hydrogen, $R_4$ is β-amino, and $R_5$ is hydrogen, which compound is in free base or acid addition salt form.

12. A compound of claim 1 where X and Y together are —O—, $R_1$ is cyclopropylmethyl, $R_2$ is ethyl, $R_3$ is hydrogen, $R_4$ is α-3-methoxycarbonylacrylamido, and $R_5$ is hydrogen, which compound is in free base or acid addition salt form.

13. a compound of claim 1 where X and Y together are —O—, $R_1$ is cyclopropylmethyl, $R_2$ is ethyl, $R_3$ is hydrogen $R_4$ is β-3-methoxycarbonylacrylamido, and $R_5$ is hydrogen, which compound is in free base or acid addition salt form.

14. a compound of claim 1 where X and Y together are —O—, $R_1$ is cyclopropylmethyl, $R_2$ is ethyl, $R_3$ is hydrogen, $R_4$ is α-3-methoxycarbonylpropionamido, and $R_5$ is hydrogen, which compound is in free base or acid addition salt form.

15. A compound of claim 1 where X and Y together are —O—, $R_1$ is cyclopropylmethyl, $R_2$ is ethyl, $R_3$ is hydrogen, $R_4$ is β-3-methoxycarbonylpropionamido, and $R_5$ is hydrogen, which compound is in free base or in acid addition salt form.

16. a compound of claim 1 where X and Y together are —O—, $R_1$ is cyclopropylmethyl, $R_2$ is ethyl, $R_3$ is β-methyl, $R_4$ is α-hydroxy, and $R_5$ is hydrogen, which compound is in free base or in acid addition salt form.

17. A compound of claim 1 where X and Y together are —O—, $R_1$ is cyclopropylmethyl, $R_2$ is ethyl, $R_3$ is α-methyl, $R_4$ is β-hydroxy, and $R_5$ is hydrogen, which compound is in free base or in acid addition salt form.

18. A compound of claim 1 where X and Y together are —O—, $R_1$ is cyclopropylmethyl, $R_2$ is ethyl, $R_3$ is β-n-butyl, $R_4$ is α-hydroxy, and $R_5$ is hydrogen, which compound is in free base or in acid addition salt form.

19. A compound of claim 1 where X and Y together are —0—, $R_1$ is cyclopropylmethyl, $R_2$ is ethyl, $R_3$ is β-phenyl, $R_4$ is α-hydroxy, and $R_5$ is hydrogen, which compound is in free base or in acid addition salt form.

* * * * *